(12) United States Patent
Xu et al.

(10) Patent No.: US 9,789,198 B2
(45) Date of Patent: Oct. 17, 2017

(54) LOW MOLECULAR WEIGHT POLYETHYLENE GLYCOL DRUG CONJUGATES HAVING IMPROVED DRUG BIOLOGICAL ACTIVITY

(71) Applicant: JENKEM TECHNOLOGY CO., LTD. (TIANJIN), Tianjin (CN)

(72) Inventors: Lihua Xu, Beijing (CN); Xuan Zhao, Beijing (CN); Zewang Feng, Beijing (CN); Jinliang Wang, Beijing (CN); Zhenguo Wang, Beijing (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 0 days.

(21) Appl. No.: 14/954,785

(22) Filed: Nov. 30, 2015

(65) Prior Publication Data

US 2016/0082117 A1   Mar. 24, 2016

Related U.S. Application Data

(63) Continuation of application No. PCT/CN2014/000550, filed on Jun. 3, 2014.

(30) Foreign Application Priority Data

May 31, 2013   (CN) .......................... 2013 1 0215297

(51) Int. Cl.
| | | |
|---|---|---|
| *A61K 31/09* | (2006.01) | |
| *A61K 47/48* | (2006.01) | |
| *A61K 31/4045* | (2006.01) | |
| *A61K 31/506* | (2006.01) | |
| *A61K 31/382* | (2006.01) | |
| *A61K 31/00* | (2006.01) | |

(52) U.S. Cl.
CPC ........ *A61K 47/48215* (2013.01); *A61K 31/00* (2013.01); *A61K 31/382* (2013.01); *A61K 31/4045* (2013.01); *A61K 31/506* (2013.01)

(58) Field of Classification Search
USPC ................................ 424/78.17, 426; 514/283
See application file for complete search history.

(56) References Cited

U.S. PATENT DOCUMENTS 6,011,042 A * 1/2000 Greenwald .......... C07D 519/00
                                                                514/283

FOREIGN PATENT DOCUMENTS

| CN | 103289075 B | 1/2016 | |
|---|---|---|---|
| WO | WO 2005/058367 A2 * | 6/2005 | ............. A61K 47/48 |

OTHER PUBLICATIONS

Pharmaceutical Solutions for Oral Administration (Chapter 1, pp. 1-24, Jul. 5, 2008).*
SIPO Office Action for CN104208715 (priority application), dated Mar. 3 2016.

* cited by examiner

*Primary Examiner* — Pancham Bakshi
(74) *Attorney, Agent, or Firm* — Zareefa B. Flener; Flener IP Law

(57) ABSTRACT

Provided are polyethylene glycol drug conjugates of general formula (I), (II) or (III) and pharmaceutical compositions and a use thereof. The conjugates are formed by combining low molecular weight polyethylene glycol with 2-4 drug molecules. The conjugates can interact with receptor dimers or polymers, thereby improving the in vivo distribution of the drug, changing the oil and water distribution coefficient, enhancing the pharmacological activity, reducing the blood-brain barrier permeability of the drug, and improving the bioavailability of the drug.

7 Claims, 1 Drawing Sheet

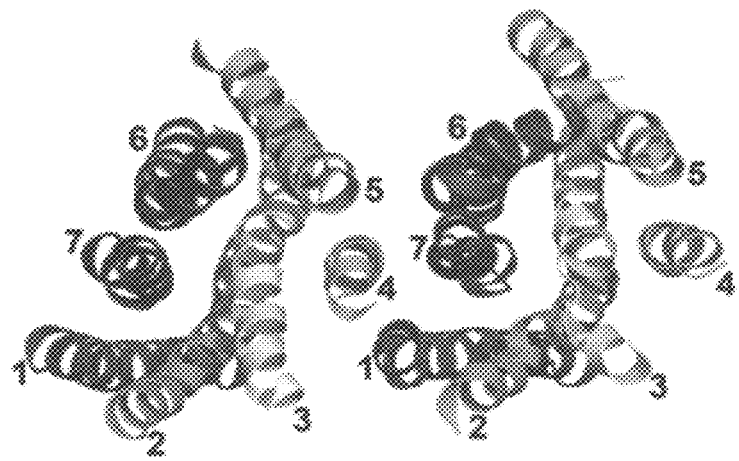

US 9,789,198 B2

LOW MOLECULAR WEIGHT POLYETHYLENE GLYCOL DRUG CONJUGATES HAVING IMPROVED DRUG BIOLOGICAL ACTIVITY

CROSS-REFERENCE TO RELATED APPLICATION

The application is a continuation of PCT/CN2014/000550 (filed on Jun. 3, 2014), which claims priority from CN Patent Application Serial No. 201310215297.9 (filed on May 31, 2013), the entire contents of which are incorporated herein by reference for all purposes.

FIELD OF THE INVENTION

The present invention relates to low molecular weight polyethylene glycol drug conjugates and application thereof, and specifically to a conjugate formed by combining low molecular weight polyethylene glycol with two or more drug molecules, and application thereof.

BACKGROUND OF THE INVENTION

Blood-brain barrier (BBB) is an important structure consisting of brain microvessel endothelial cell and a basement membrane closely connected thereto and astrocyte foot processes around the blood vessels. A main function thereof is to maintain stability of an environment in a central nervous system and a normal function of neuron. The brain microvessel endothelial cell is to some extent distinct from endothelial cells of other blood vessels of an organism in terms of gene constitution and morphological structure, and on its cell membrane are distributed various protein and transporters maintaining its special selective permeability.

The capability of a drug penetrating BBB is usually related to relative molecular mass, fat solubility, charge property of the drug itself and its bonding capability with plasma protein and a special carriers or receptor transport system. In addition to water, electrolyte and partial macromolecular substances which may pass freely, most drugs (such as levodopa, codein etc.) that may penetrate the BBB are transported into brain via vector mediation. Its mechanism comprises facilitated diffusion, active transport and pinocytosis. It is difficult for hydrophilic and macromolecular drugs themselves to penetrate the BBB. Some lipophilic drugs with suitable molecular weight can penetrate the BBB, but they are apt to be transported by an efflux pump by P glycoprotin (P-gp) on the BBB so that effective drugs in the brain have a low concentration and act in a short time period.

Many drugs have a very good efficacy, but the high blood-brain barrier permeability causes large toxicity and side effects to the central nervous system. Upon studying these drugs, main thoughts are given to reduction of the blood-brain barrier permeability as well as maintenance or improvement of drug efficacy. There are many methods of reducing the blood-brain barrier permeability. The present invention reduces the blood-brain barrier permeability and achieves an effect of reducing toxicity and side effects and maintaining activity mainly by modifying polyethylene glycol, introducing low molecular weight polyethylene glycol into the compound structure to increase its hydrophilicity.

Polyethylene glycol (PEG) modification technology is a new drug delivery technology which has developed rapidly in recent years and is a technology linking activated polyethylene glycol to a drug molecule or surface. After combining with the polyethylene glycol, pharmacokinetics of the drug changes and thereby pharmacodynamics changes so that the drug in vivo activity is improved. At present, polyethylene glycol (PEG) technology has already been extensively applied to modification of protein drugs and becomes an important means for improving clinical effects of the protein drugs. Currently, there are eleven polyethylene glycol drug products in the international market, wherein annual sales amount of PEG-intron®, PEGasys®, Neulasta® or Macugen® exceeds 100 million US dollars, and annual sales amount of PEGasys® and Neulasta® is 1.8 billion US dollars and 3.6 billion US dollars respectively. In recent years, polyethylene glycol (PEG) modification technology has already spread from protein drugs to small molecule drugs. Small molecules of the drugs, after being modified by polyethylene glycol, mainly have the following advantages: 1) increase drug water-solubility; 2) change oil-water distribution coefficient; 3) prolong cyclic half-life of the drug, reduce times of administration, improve patient compliance and life quality and reduce treatment fees; 4) reduce enzyme degradation and improve bioavailability. However, generally, in vitro activity of the drug after polyethylene glycol (PEG) modification substantially reduces. For example, the activity of PEGasys® in vitro is only about 2 percent of interferon. While using advantages of polyethylene glycol (PEG) modification (e.g., increase water-solubility and reduce blood-brain barrier permeability), maintaining or improving the bioactivity of the drug in vitro is a problem of polyethylene glycol (PEG) modification technology need to be solved urgently, Meanwhile, most drugs effect by interacting with a specific receptor in vivo and changing physiological and biochemical function of cells. Currently, there are tens of already-determined receptors, wherein functions of cells of a majority of organisms are all identified by membrane receptors, and wherein main membrane receptors belong to G Protein-Coupled Receptor (GPCR) family. It is believed that GPCR exists mainly in the form of a monomer, which is coupled to G protein to produce identification of a ligand and mediate conduction of a series of signals. In recent years, research of GPCR indicates that GPCR may exist in the form of a dimer and a polymer. For example, opium receptor, $\beta_2AR$, dopamine receptor, chemotactic factor receptor, mGluR5, extracellular $Ca^{2+}$ sensitive receptor all can form a dimer and polymer. The dimer comprises homodimer and heterodimer. FIG. 1 shows a 3-D structure of a heterodimer of Mu-delta opioid peptide receptor.

In consideration with reduction of blood-brain barrier permeability and inspiration of receptor dimers and polymers, we designed a class of compounds with a new structure by using properties of small-molecule polyethylene glycol, with the reference to the double group structure of the natural antibody in organism. Said compounds are characterized in that an end of small-molecule polyethylene glycol is combined with two more drug molecules in the form of a chemical bond to form a double-group or multi-group structure of a similar antibody. Hydrophilicity of oxygen atoms in polyethylene glycol fragments and space flexibility of linear-chained alkoxy increases possibility of the new compounds binding with the receptor dimer or multimer and improves drug activity; meanwhile, as molecular weight increases, hydrophilicity increases, in vivo distribution changes, blood-brain barrier permeability of the drug falls, and the side effects to the central system decrease. Furthermore, introduction of small-molecule polyethylene glycol causes changes of the oil-water distribution coefficient of the new compounds and increase of water-solubility, some drugs that cannot be taken orally can be produced as oral drugs.

In early-stage experimental research of the laboratory, Patent CN201110393196.1 disclosed a method of low molecular weight polyethylene glycol to combine with tamsulosin by chemical bond. Patent US2005136031A1 disclosed a method of linking polyethylene glycol having one closed end with naloxone. Patent CN201210040133.2 disclosed a method of linking naloxone with low molecular weight polyethylene glycol. Pharmacological results testify that activity of a product produced by linking both ends of polyethylene glycol with naloxone is higher than an single-end substitution product. However, the above work all does not carry out sufficient research for the blood-brain barrier permeability of this series of compounds.

The present invention provides a new polyethylene glycol modified drug. The polyethylene glycol modified drug is polyethylene glycol-linked drug dimer or polymer, which is obtained by the method of deriving end groups of low molecular weight polyethylene glycol having two or more end groups, and combining them with the drug molecules. The new compounds exhibit increased drug activities in vitro, increase of solubilities, changes of oil-water distribution coefficient, changes of distribution in vivo, reduction of blood-brain barrier permeability and finally rise of the effect in vivo.

SUMMARY OF THE INVENTION

According to an aspect of the present invention, it provides a drug-polyethylene glycol-drug conjugate of formula (I), the conjugate being formed by combining low molecular weight polyethylene glycol with two drug molecules,

TA-X-PEG-X'-TA' (I)

Wherein PEG is a polyethylene glycol residue having the following structure,

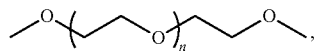

Wherein n is an integer of 0-25; X, X' are linking groups which may be same or different, selected from a group consisting of

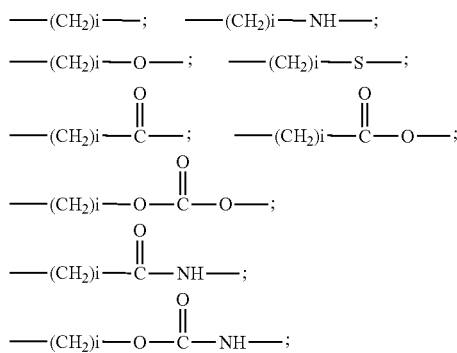

i is an integer of 0-10; TA, TA' are target compounds that may be same or different, selected from a group consisting of small molecule drugs which structures include hydroxyl, amino, sulfonamido, amide or thiol group, such as sumatriptan, dorzolamide, irinotecan, camptothecin, dasatinib, paclitaxel, docetaxel, cyclovirobuxinum D, diethylstilbestrol, estradiol, prazosin, terazosin, metoclopramide, ursodesoxycholic acid, rapamycin, scopolamine.

In an embodiment, n is an integer of 0-10. Preferably, n is 0, 1, 2, 3, 4, 5, 6, 7, 8, 9, 10 or a range of any two integers thereof.

In another embodiment, i=2, and X, same as X', is —(CH$_2$CH$_2$)O—.

In a further embodiment, TA is the same as TA', selected from a group consisting of sumatriptan, dorzolamide and dasatinib.

According to an aspect of the present invention, it provides a polyethylene glycol-(drug)$_3$ conjugate of formula (II), the conjugate being formed by combining low molecular weight polyethylene glycol with three drug molecules,

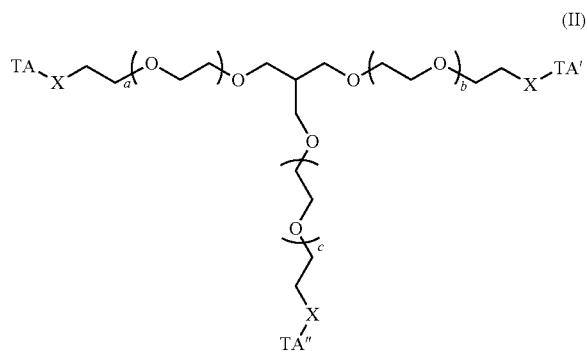

Wherein a, b and c may be identical or different and is an integer of 0-20; X is a linking group, selected from a group consisting of

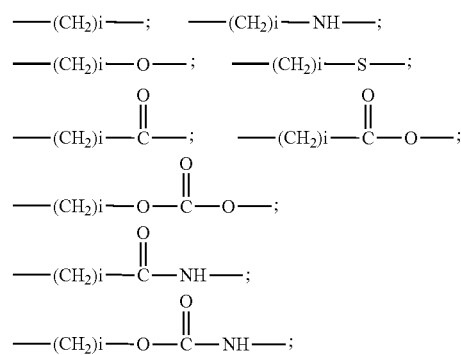

i is an integer of 0-10; TA, TA', TA" are target compounds that may be identical or different, selected from a group consisting of small molecule drugs which structures include hydroxyl, amino, sulfonamido, amide or thiol group, such as sumatriptan, dorzolamide, irinotecan, camptothecin, dasatinib, paclitaxel, docetaxel, cyclovirobuxinum D, diethylstilbestrol, estradiol, prazosin, terazosin, metoclopramide, ursodesoxycholic acid, rapamycin, scopolamine, procaine.

In an embodiment, a, b and c are identical and an integer of 0-10. Preferably, a, b, c are 0, 1, 2, 3, 4, 5, 6, 7, 8, 9, 10 or a range of any two integers thereof.

In another embodiment, X is —(CH$_2$CH$_2$)O—.

In a further embodiment, TA, TA' and TA" all are dorzolamide.

According to an aspect of the present invention, it provides a polyethylene glycol-(drug)$_4$ conjugate of formula (III), the conjugate being formed by combining low molecular weight polyethylene glycol with four drug molecules, According to a further aspect of the present invention, the present invention provides a drug composition including said conjugate and a pharmaceutically acceptable carrier or excipient.

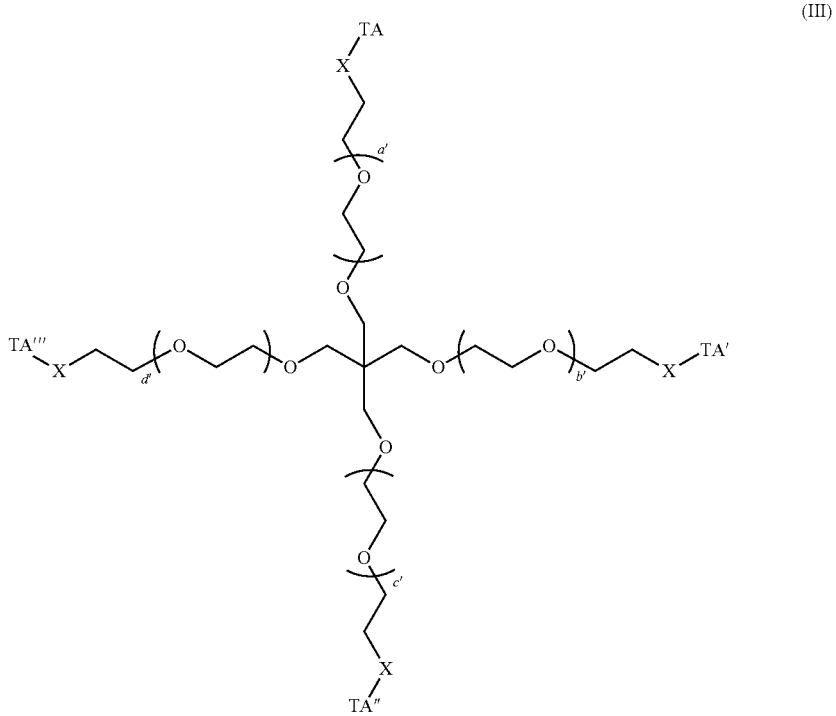

(III)

Wherein a', b', c' and d' may be identical or different and be an integer of 0-20; X is a linking group, selected a group consisting of

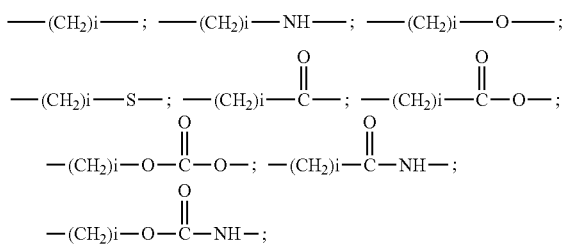

i is an integer of 0-10;
TA, TA', TA" and TA'" are target compounds that may be identical or different, selected from a group consisting of small molecule drugs which structures include hydroxyl, amino, sulfonamido, amide or thiol group, such as sumatriptan, dorzolamide, irinotecan, camptothecin, dasatinib, paclitaxel, docetaxel, cyclovirobuxinum D, diethylstilbestrol, estradiol, prazosin, terazosin, metoclopramide, ursodesoxycholic acid, rapamycin, scopolamine, procaine.

Wherein in an embodiment, a', b', c' and d' are identical and an integer of 0-10. Preferably, a', b', c', d' are 0, 1, 2, 3, 4, 5, 6, 7, 8, 9, 10 or a range of any two integers thereof.

In another embodiment, X is —(CH$_2$CH$_2$)O—.

In a further embodiment, TA, TA', TA" and TA'" all are dorzolamide.

According to a further aspect of the present invention, the present invention provides a drug composition including said conjugate and a pharmaceutically acceptable salt, wherein the pharmaceutically acceptable salt is selected from a group consisting of hydrochloride, hydrobromate, sulphate, nitrate, phosphate, citrate, tartrate, fumarate, maleate, lactate, benzene sulfonate, pantothenate, ascorbate or combinations thereof, and wherein the drug composition is in the form of tablet, suppository, pill, soft and hard gelatin capsule, powder, solution, suspension or aerosol.

According to a further aspect of the present invention, the present invention provides the use of said conjugate in drug preparation.

According to a further aspect of the present invention, the present invention provides a polyethylene glycol (PEG) modification method for improving small molecule drug performance, reducing blood-brain barrier permeability, and maintaining or improving drug activity by means of low molecular weight polyethylene glycol, and its preparation method and application. The compound having a new structure may interact with receptor dimer or polymer to produce an effect, improve drug in vivo distribution, change oil-water distribution coefficient, enhance drug activity, reduce drug blood-brain barrier permeability, and improve drug bioavailability.

According to a further aspect of the present invention, the present invention provides a method for preparing a conjugate by combining small molecule drugs which include hydroxyl, amino, sulfonamido, amide or thiol groups with low molecular weight polyethylene glycol, wherein small molecule drugs are selected from sumatriptan, dorzolamide, irinotecan, camptothecin, dasatinib, paclitaxel, docetaxel, cyclovirobuxinum D, diethylstilbestrol, estradiol, prazosin, terazosin, metoclopramide, ursodesoxycholic acid, rapamycin, scopolamine, procaine.

BRIEF DESCRIPTION OF DRAWINGS

FIG. 1 is a view showing a 3-D structure of a heterodimer of Mu-delta opioid peptide receptor.

DETAILED DESCRIPTION OF THE INVENTION

Polyethylene glycol units are used to indicate low polyethylene glycol. Generally, the number of the included polyethylene glycol units is used to indicate low polyethylene glycol, the number of polyethylene glycol units is an integer of 0-20, preferably an integer of 3-10.

The polyethylene glycol in the present invention includes derivatives and analogues of polyethylene glycol and may be substituted by one of the following hydrophilic polymers, which is selected from a group consisting of polyethylene glycol, polyglutamic acid, polyaspartic acid, polypropylene glycol, polyvinyl alcohol, polypropylene morpholine, polyoxazolone and copolymers thereof.

The conjugate of the present invention may be administered in a form of a pure compound or a suitable drug composition, in any acceptable administration manner, or used for a reagent with similar use. Therefore, the employed administration manner may be selected from oral administration, intranasal administration, non-intestinal administration, local administration, percutaneous administration or rectum administration, administration takes a form of solid, semisolid or liquid medicament, e.g., tablet, suppository, pill, soft and hard gelatin capsule, powder, solution, suspension or aerosol, and preferably employs a unit dosage enabling simple administration with an accurate dosage. The composition may include a conventional drug carrier or excipient and the conjugate of the present invention as an active component (one or more kinds), and additionally may comprise other medicaments, carriers, adjuvants and the like.

Usually, according to the desired administration manner, the pharmaceutically acceptable composition will include about 1 to 99 weight percent conjugate of the present invention, and 99-1 weight percent suitable medical excipient. Preferably, the composition includes about 5-75 weight percent conjugate of the present invention, with the balance being a suitable medical excipient.

According to the drug composition that may be administered in form of a liquid, for example, the conjugate (about 0.5-about 20%) of the present invention and selectively-existing medicinal adjuvants are solved and dispersed in a carrier by a solving and dispersing means to form a solution or suspension, wherein examples of the carrier is water, saline, glucose hydrate, glycerol, ethanol or the like.

If necessary, the drug composition of the present invention may further include a small amount of assistant substance such as a wetting agent or emulsifier, pH buffering agent, and antioxidant, for example, citric acid, sorbitan monolaurate, trithanolamine oleate, butylated hydroxytoluene.

The following examples are used to illustrate the present invention, but not used to limit the present invention.

Sumatriptan used in the examples are provided by Jiangsu Ocean Biological Engineering Co., Ltd, dasatinib is provided by Nanjing Ange Pharmaceutical and Chemical Co., Ltd, metoxyethoxymethyl chloride (MEMCL) is provided by Alfa Aesar, paratoluensulfonyl chloride is purposed from Shandong Yilong Industrial Co., Ltd, sodium hydride is purchased from TCI (Shanghia) Chemical Industry Development Co., Ltd., and $H(OCH_2CH_2)_4$—OH, $H(OCH_2CH_2)_6$—OH and $H(OCH_2CH_2)_{12}$—OH are purchased from Jiaxing Bomei Biotechnology Co., Ltd. Other reagents used in examples of the present invention all are reagents available in the market.

Examples

Example 1 Synthesis of Double End-Substituted Hexaethyleneglycol-Sumatriptan (SMQT-01)

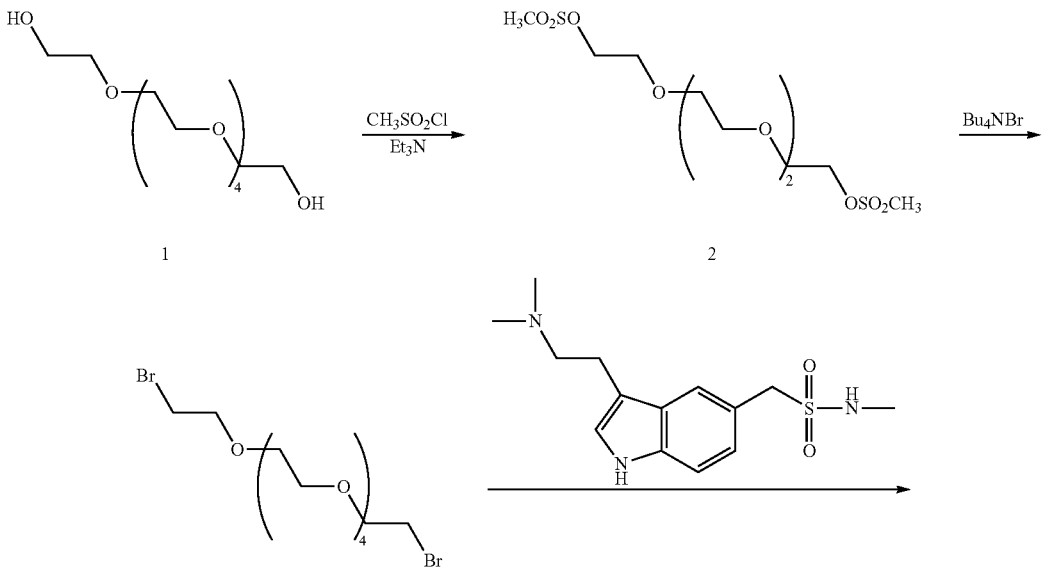

-continued

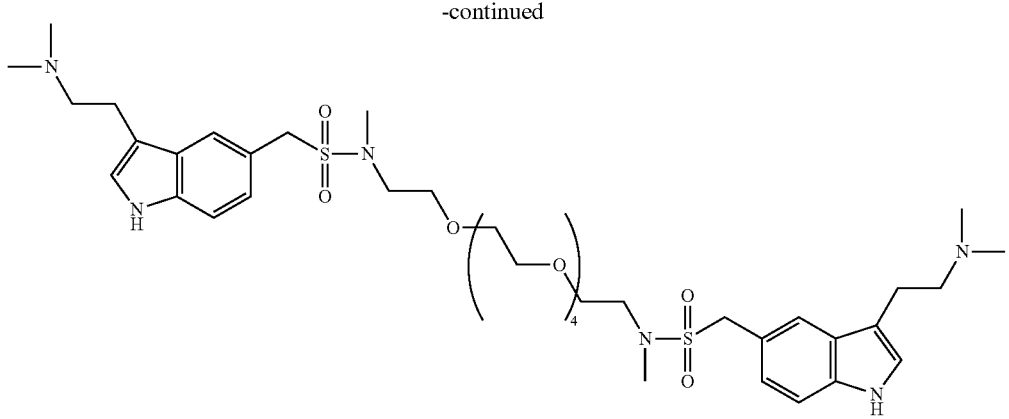

4

Hexaethyleneglycol (1) (2.5 ml, 10 mmol) is dissolved in 50 mL dichloromethane, triethylamine (4.17 ml, 10 mmol) is added, methanesulfonyl chloride (1.72 mL, 22 mmol) is dripped in, and reaction continues 16 hours at a room temperature under nitrogen gas protection. 1.2 ml methanol is added and stirred 15 minutes, filtering is performed to remove solid to concentrate to obtain 3.85 g product (2), with a yield rate 99%, which is directly used for next reaction.

Hexaethyleneglycol disulfonate (2) (3.85 g, 10 mmol) and 13.3 g tetrabutyl ammonium bromide are dissolved in acetonitrile 50 mL, and stirred and react 16 hours under nitrogen gas protection. Solvent is evaporated out, acetic ether and water are added for extraction, extract is dried by using anhydrous sodium sulfate, concentrates and goes through column separation to obtain 2.85 g product (3), with a yield rate 80%. $^1$H-NMR (CDCl$_3$): 3.82 (t, 4H), 3.67 (s, 16H), 3.48 (t, 4H).

Sumatriptan (236 mg, 0.8 mmol) is dissolved in 2 mL dry DMF, 60% NaH (32 mg, 0.8 mmol) is added, stirred and react 15 minutes, then the compound (3) (163.2 mg, 0.4 mmol) is added, and reaction is performed overnight under nitrogen gas protection. Water is added to the above reaction liquid to quench the reaction, extraction is performed three times by using acetic ether, an organic phase is dried by using anhydrous sodium sulfate, concentrate goes through column separation to obtain 240 mg product, with a yield rate 61%. $^1$H-NMR (CDCl$_3$): 2.34 (s, 12H), 2.63 (t, 4H), 2.77 (s, 6H), 2.93 (t, 4H), 3.13 (t, 4H), 3.44 (t, 4H), 3.51 (s, 16H), 4.34 (s, 4H), 6.98 (s, 2H), 7.14 (d, 2H), 7.26 (d, 2H), 7.57 (s, 2H), 8.91 (s, 2H).

Example 2 Synthesis of Double End-Substituted Pentaethyleneglycol-Sumatriptan (SMQT-02)

Pentaethyleneglycol (2.38 g, 10 mmol) is dissolved in 50 mL dichloromethane, triethylamine (4.16 ml, 10 mmol) is added, methanesulfonyl chloride (1.77 mL, 22 mmol) is dripped in, and reaction continues 16 hours at a room temperature under nitrogen gas protection. 1.2 ml methanol is added and stirred 15 minutes, filtering is performed to remove solid to concentrate to obtain 3.94 g product, with a yield rate 99%, which is directly used for next reaction.

Pentaethyleneglycol disulfonate (3.94 g, 10 mmol) and 13.3 g tetrabutyl ammonium bromide are dissolved in acetonitrile 50 mL, and stirred and react 16 hours under nitrogen gas protection. Solvent is evaporated out, acetic ether and water are added for extraction, extract is dried by using anhydrous sodium sulfate, concentrates and goes through column separation to obtain 2.73 g product, with a yield rate 75%. $^1$H-NMR (CDCl$_3$): 3.49 (t, 4H), 3.69 (s, 12H), 3.84 (t, 4H).

Sumatriptan (236 mg, 0.8 mmol) is dissolved in 2 mL dry DMF, 60% NaH (32 mg, 0.8 mmol) is added, stirred and react 15 minutes, triethylene glycol 2-bromoethyl (145.6 mg, 0.4 mmol) is added, and reaction is performed overnight under nitrogen gas protection. Water is added to the above reaction liquid to quench the reaction, extraction is performed three times by using acetic ether, an organic phase is dried by using anhydrous sodium sulfate, concentrate goes through column separation to obtain 184 mg product, with a yield rate 58%. $^1$H-NMR (CDCl$_3$): 2.34 (s, 12H), 2.70 (t, 4H), 2.72 (s, 6H), 2.94 (t, 4H), 3.06 (t, 4H), 3.40 (t, 4H), 3.49 (s, 12H), 4.35 (s, 4H), 6.98 (s, 2H), 7.11 (d, 2H), 7.23 (d, 2H), 7.60 (s, 2H), 8.91 (s, 2H).

Example 3 Synthesis of Double End-Substituted Triethylene Glycol-Sumatriptan (SMQT-03)

Triethyleneglycol (2.67 ml, 20 mmol) is dissolved in 50 mL dichloromethane, triethylamine (8.33 mL, 20 mmol) is added, methanesulfonyl chloride (3.44 mL, 44 mmol) is dripped in, and reaction continues 16 hours at a room temperature under nitrogen gas protection. 1.2 ml methanol is added and stirred 15 minutes, filtering is performed to remove solid to concentrate to obtain 6.12 g product, with a yield rate 99%, which is directly used for next reaction.

Triethyleneglycol disulfonate (4.12 g, 13.46 mmol) and 17.3 g tetrabutyl ammonium bromide are dissolved in acetonitrile 50 mL, and stirred and react at 50° C. 16 hours under nitrogen gas protection. Solvent is evaporated out, acetic ether and water are added for extraction, extract is dried by using anhydrous sodium sulfate, concentrates and goes through column separation to obtain 2.84 g product, with a yield rate 77%. $^1$H-NMR (CDCl$_3$): 3.49 (t, 4H), 3.70 (s, 4H), 3.84 (t, 4H).

Sumatriptan (236 mg, 0.8 mmol) is dissolved in 2 mL dry DMF, 60% NaH (32 mg, 0.8 mmol) is added, stirred and react 15 minutes, then ethylene glycol 2-bromoethyl (109.6 mg, 0.4 mmol) is added, and reaction is performed overnight under nitrogen gas protection. Water is added to the above reaction liquid to quench the reaction, extraction is performed three times by using acetic ether, an organic phase is dried by using anhydrous sodium sulfate, concentrate goes through column separation to obtain a product, with a yield rate 61%. $^1$H-NMR (CDCl$_3$): 2.35 (s, 12H), 2.66 (t, 4H), 2.72 (s, 6H), 2.94 (t, 4H), 3.07 (t, 4H), 3.40 (t, 4H), 3.47 (s, 4H), 4.34 (s, 4H), 6.98 (s, 2H), 7.12 (d, 2H), 7.23 (d, 2H), 7.60 (s, 2H), 8.91 (s, 2H).

Example 4 Synthesis of Double End-Substituted Tetraethylene Glycol-Dasatinib (DSTN-42)

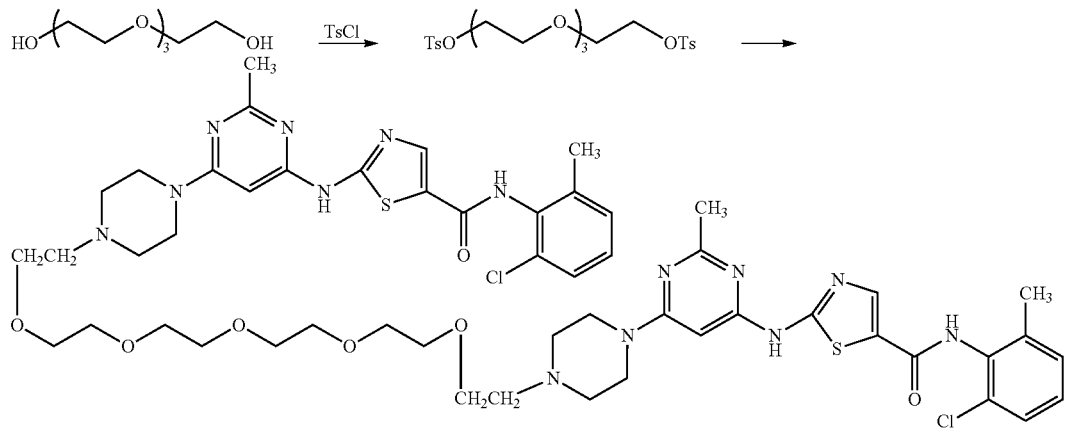

19.1 g paratoluensulfonyl chloride and 40 mL pyridine are added in 250 mL three-neck flask, and cooled to 0° C. 9.7 g HO-PEG(n=4)-OH is mixed uniformly with 20 mL pyridine, and then dripped in the three-neck flash, and the temperature is controlled between 0 and 10° C. Stirring and reaction is continued at this temperature for two hours. TLC monitors that the reaction is complete. 300 mL cold water and 60 mL concentrated hydrochloric acid are added in the reaction liquid and slowly stirred for half an hour, then the reaction liquid is transferred into a 500 mL separating funnel, acetic ether is added to extract twice (300 mL+200 mL). The organic layers are merged and washed by water to neutrality, dried by anhydrous sodium sulfate for two hours. A rotary evaporator evaporates out solvent to obtain 21.4 g viscous liquid, which will be directly used for next reaction.

487 g dasatinib and 166 mg potassium carbonate are added into a 100 mL three-neck flask filled with 20 mL acetonitrile, and stirred at a room temperature for two hours. 10 mL acetonitrile solution in which 258 mg TsO-PEG(n=4)-OTs is dissolved is added to the reaction flask, and reflex reacts overnight. TLC monitors that the reaction is complete. Column separation is carried out to obtain 308 mg white solid with a yield rate 54.5%. m/z [MH]$^+$1133. $^1$H-NMR (DMSO-d6): 2.23 (s, 6H), 2.49 (s, 6H), 2.51 (m, 8H), 3.53 (m, 32H), 6.04 (s, 2H), 7.27 (m, 4H), 7.40 (m, 2H), 8.22 (s, 2H), 9.88 (s, 2H), 11.48 (s, 2H).

9.6 g paratoluensulfonyl chloride and 40 mL pyridine are added in 250 mL three-neck flask, and cooled to 0° C. 12.6 g mPEG(n=5)-OH is mixed uniformly with 20 mL pyridine, and then dripped in the three-neck flash, and the temperature is controlled between 0 and 10° C. Stirring and reaction is continued at this temperature for two hours. TLC monitors that the reaction is complete. 300 mL cold water and 60 mL concentrated hydrochloric acid are added in the reaction liquid and slowly stirred for half an hour, then the reaction liquid is transferred into a 1000 mL separating funnel, acetic ether is added to extract twice (300 mL+200 mL). The organic layers are merged and washed by water to neutrality, dried by anhydrous sodium sulfate for two hours. A rotary evaporator evaporates out solvent to obtain 21.5 g viscous liquid, which will be directly used for next reaction.

253 g dasatinib and 128 mg potassium carbonate are added into a 100 mL three-neck flask filled with 20 mL acetonitrile, and stirred at a room temperature for two hours. 10 mL acetonitrile solution in which 205 mg mPEG(n=5)OTs is dissolved is added to the reaction flask, and reflex reacts overnight. TLC monitors that the reaction is complete. Column separation is carried out to obtain 205 mg white solid with a yield rate 56.8%. m/z [MH]$^+$722. $^1$H-NMR (DMSO-d6): 2.24 (s, 3H), 2.43 (s, 3H), 2.51 (m, 8H), 3.22 (s, 3H), 3.61 (m, 20H), 6.05 (s, 1H), 7.27 (m, 2H), 7.41 (m, 1H), 8.22 (s, 1H), 9.88 (s, 1H), 11.48 (s, 1H).

Example 5 Synthesis of Methoxyl Pentaethylene Glycol-Dasatinib (DSTN-51)

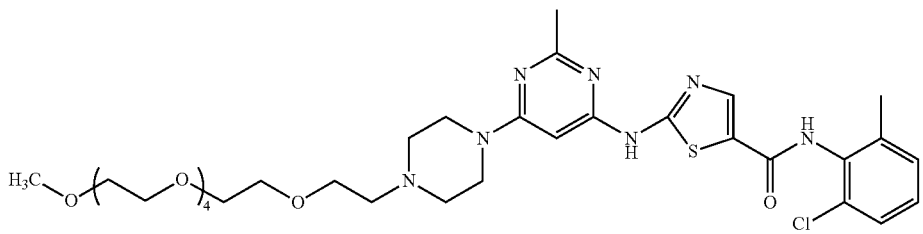

Example 6 Synthesis of Double End Hexaethylene Glycol-Dasatinib (DSTN-62)

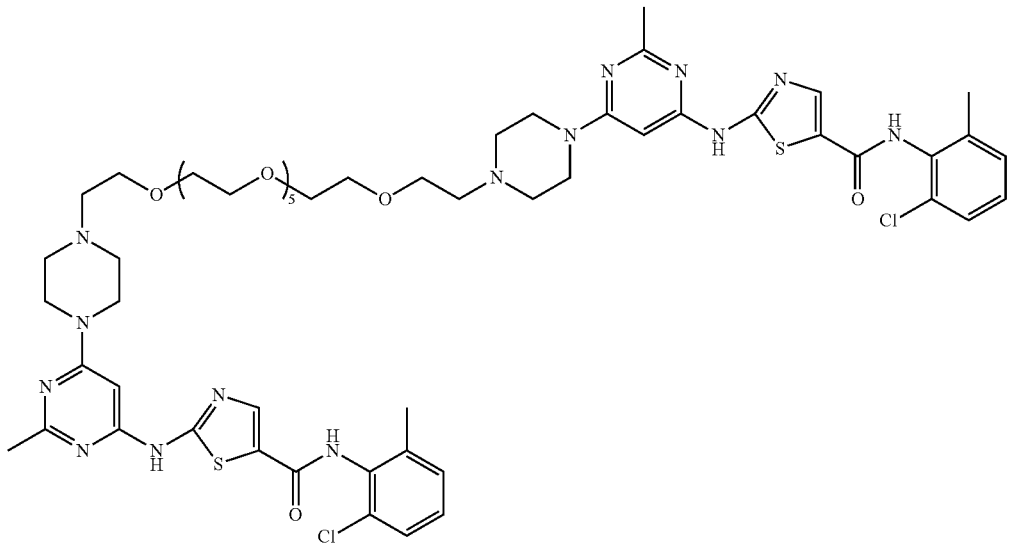

19.1 g paratoluensulfonyl chloride and 40 mL pyridine are added in 500 mL three-neck flask, and cooled to 0° C. 14.1 g HO-PEG(n=6)-OH is mixed uniformly with 20 mL pyridine, and then dripped in the three-neck flash, and the temperature is controlled between 0 and 10° C. Stirring and reaction is continued at this temperature for two hours. TLC monitors that the reaction is complete. 300 mL cold water and 60 mL concentrated hydrochloric acid are added in the reaction liquid and slowly stirred for half an hour, then the reaction liquid is transferred into a 1000 mL separating funnel, acetic ether is added to extract twice (300 mL+200 mL). The organic layers are merged and washed by water to neutrality, dried by anhydrous sodium sulfate for two hours. A rotary evaporator evaporates out solvent to obtain 28.7 g viscous liquid, which will be directly used for next reaction.

506 g dasatinib is dissolved in 6 ml N,N-dimethylformamide, 160 mg NaH is added, and stirred at a room temperature for one hour. 302 mg TsO-PEG(n=6)-Ots is added for reaction at a room temperature for 20 hours. TLC monitors that the reaction is complete. Column separation is carried out to obtain 316 mg white solid with a yield rate 51.8%. m/z [MH]$^+$1221. $^1$H-NMR (DMSO-d6): 2.19 (s, 6H), 2.28 (s, 6H), 2.49 (m, 8H), 3.61 (m, 40H), 6.04 (s, 2H), 7.20 (m, 4H), 7.41 (m, 2H), 8.18 (s, 2H), 9.87 (s, 2H), 11.46 (s, 2H).

Example 7 Single End Substituted Pentaethyleneglycol-Dorzolamide (DZA-01)

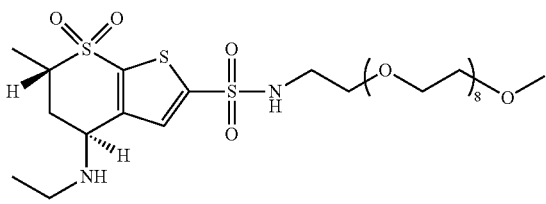

Nonaethyleneglycol monomethyl (4.28 g, 10 mmol) is dissolved in 50 mL dichloromethane, triethylamine (4.16 ml, 10 mmol) is added, methanesulfonyl chloride (0.9 mL, 11 mmol) is dripped in, and reaction continues 16 hours at a room temperature under nitrogen gas protection. 1.2 ml methanol is added and stirred 15 minutes, filtering is performed to remove solid to concentrate to obtain a product, which is directly used for next reaction.

The above obtained product and 6.80 g tetrabutyl ammonium bromide are dissolved in 50 mL acetonitrile, and stirred and react at 50° C. for 16 hours under nitrogen gas protection. Solvent is evaporated out, acetic ether and water are added for extraction, extract is dried by using anhydrous sodium sulfate, concentrates and goes through column separation to obtain 3.38 g product, with a yield rate 68%.

Dorzolamide (324 mg, 1 mmol) is dissolved in 2 mL dry DMF, 60% NaH (40 mg, 1 mmol) is added, stirred and react 15 minutes, an intermediate (491 mg, 1 mmol) is added, and reaction is performed overnight under nitrogen gas protection. Water is added to the above reaction liquid to quench the reaction, extraction is performed three times by using acetic ether, an organic phase is dried by using anhydrous sodium sulfate, concentrate goes through column separation to obtain 352 mg product, with a yield rate 48%. m/z [MH]$^+$735.

Example 8 Double End Substituted Hexaethyleneglycol-Dorzolamide (DZA-02)

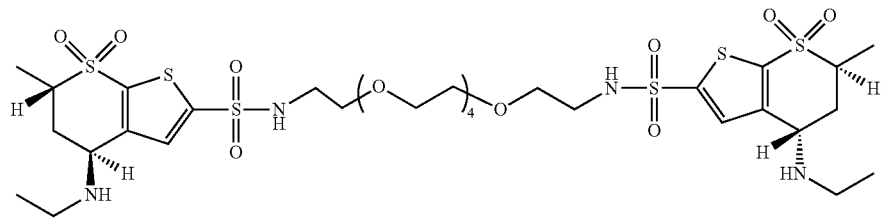

Reference is made to Example 6 for the syntheses method. m/z [MH]+895.

Example 9 Double End Substituted Odecylethyleneglycol-Dorzolamide (DZA-03)

$H(OCH_2CH_2)_{12}$—OH is used to substitute hexaethyleneglycol. Reference is made to Example 6 for the syntheses method. m/z [MH]$^+$1159.

Example 10 Three-Branch Ethyleneglycol-Dorzolamide Conjugate (DAZ-04)

Regarding syntheses of three-branch ethyleneglycol (H), please refer to US2006/0047167.

Reference is made to Example 6 for the syntheses method. m/z [MH]$^+$1157.

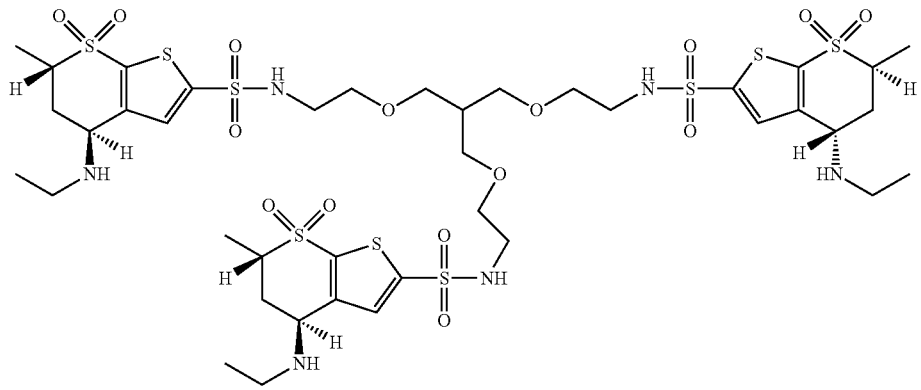 [SMILES: CCN[C@H]1C[C@H](C)S(=O)(=O)c2sc(S(=O)(=O)NCCOCC(COCCNS(=O)(=O)c3cc4c(s3)S(=O)(=O)[C@@H](C)C[C@@H]4NCC)COCCNS(=O)(=O)c3cc4c(s3)S(=O)(=O)[C@@H](C)C[C@@H]4NCC)cc21]

Example 11 Three-Branch Ethyleneglycol-Dorzolamide Conjugate (DAZ-05)

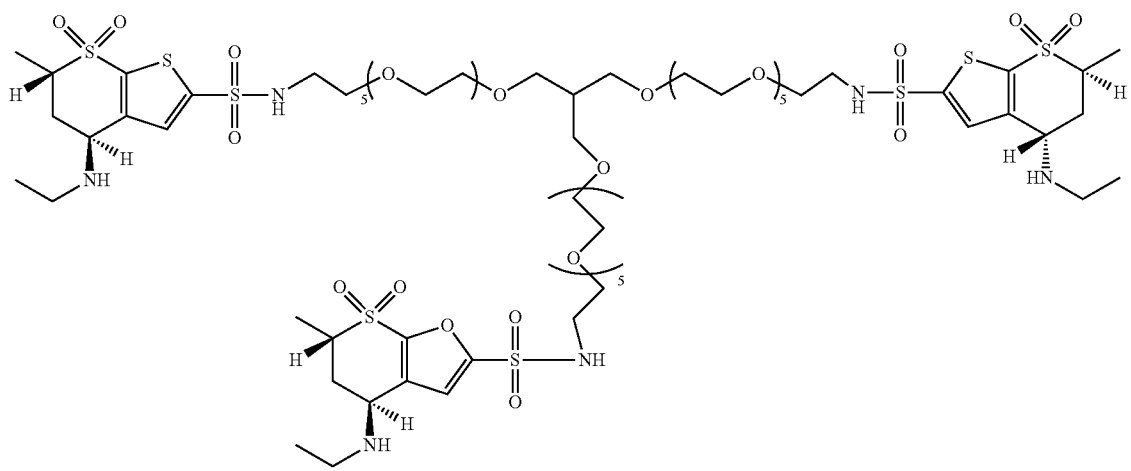

Regarding syntheses of the compound L, please refer to *J. Org. Chem.* 2006, 71, 9884-9886.

Reference is made to Example 6 for the syntheses method.
m/z [MH]⁺1818.

Example 12 Four-Branch Ethyleneglycol-Dorzolamide Conjugate (DAZ-06)

Regarding syntheses of the four-branch ethyleneglycol, please refer to Bulletin of Academy of Sciences of the USSR, Division of Chemical Science (English Translation); vol. 38; nb. 10; (1989); p. 2207.

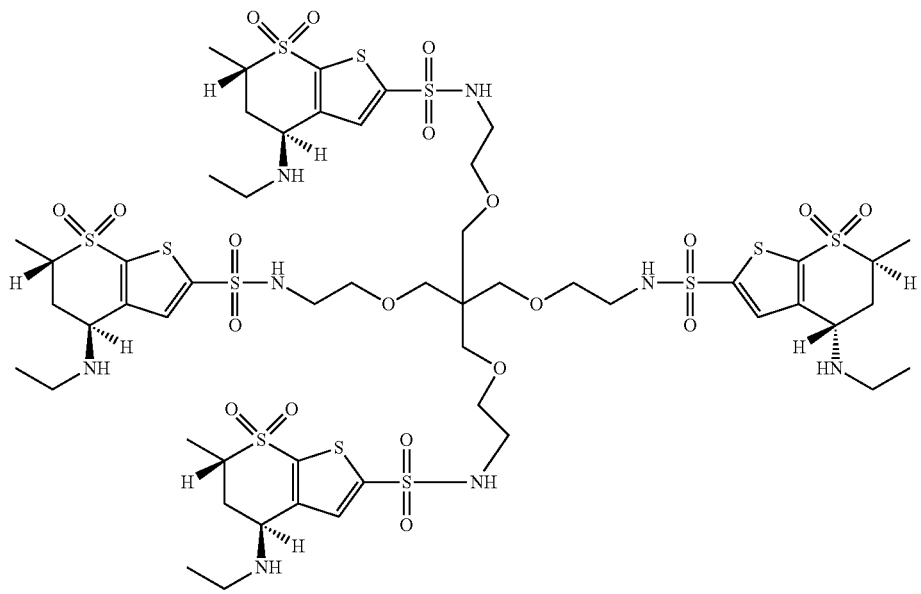 [SMILES: CCN[C@H]1C[C@H](C)S(=O)(=O)c2sc(S(=O)(=O)NCCOCC(COCCNS(=O)(=O)c3cc4c(s3)S(=O)(=O)[C@@H](C)C[C@@H]4NCC)(COCCNS(=O)(=O)c3cc4c(s3)S(=O)(=O)[C@@H](C)C[C@@H]4NCC)COCCNS(=O)(=O)c3cc4c(s3)S(=O)(=O)[C@@H](C)C[C@@H]4NCC)cc21]

Reference is made to Example 6 for the syntheses method.
m/z [MH]⁺1538.

Example 13 Four-Branch Ethyleneglycol-Dorzolamide Conjugate (DAZ-07)

Regarding syntheses of the compound R, please refer to *J. Org. Chem.* 2006, 71, 9884-9886.

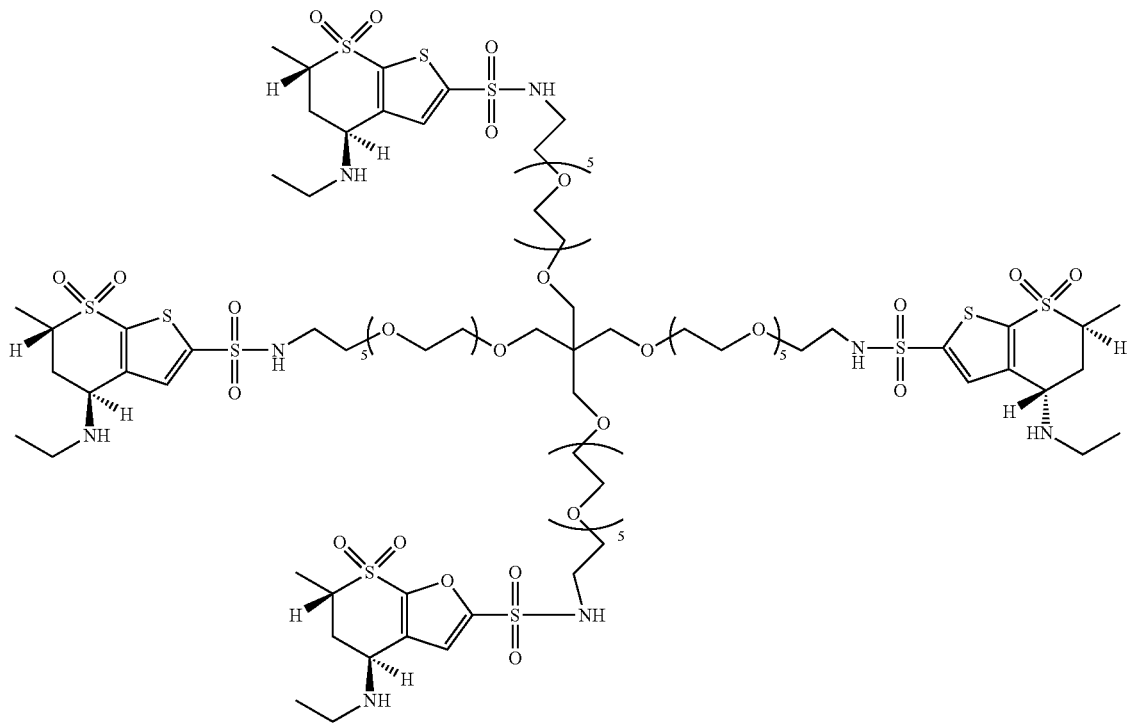

Reference is made to Example 6 for the syntheses method. m/z [MH]⁺2490.

Example 14 Inhibition of Dasatinib Series Compounds for Cell Proliferation and IC50 Measurement Research Purpose Detection is performed for the function of three kinds of drugs for proliferation of tumor cells K562, KU812, SUP-B15, and PC-3, to determine its 50% inhibition centration (IC50).

Research Scheme

Cells are cultured under a complete culture medium; when cells are attached to the wall, drug of different concentrations is added in each tumor cell line for treatment, and a positive control, a blank control and a solvent control are set. Cells are incubated for 72 hours and then CTG method is used for detection.

TABLE 1

| | IC50 (μM) results | | |
|---|---|---|---|
| Serial | | IC50 (μM) | |
| number | Cell line | DSTN-51 | DSTN-42 | DSTN-62 |
| 1 | PC-3 | 83.12 | — | — |
| 2 | SUP-B15 | 0.17 | 0.05 | 0.06 |
| 3 | K562 | 0.00222 | 0.00050 | 0.00034 |
| 4 | KU812 | 0.00050 | 0.00079 | 0.00049 |

Notes:
"—" indicates that IC50 value cannot be calculated

TABLE 2

| | Maximum inhibition rate | | |
|---|---|---|---|
| Serial | | Maximum inhibition rate (%) | |
| number | Cell line | DSTN-51 | DSTN-42 | DSTN-62 |
| 1 | PC-3 | 56.67 | 30.97 | 29.74 |
| 2 | SUP-B15 | 91.39 | 93.36 | 81.47 |
| 3 | K562 | 79.04 | 80.34 | 81.76 |
| 4 | KU812 | 96.47 | 96.91 | 96.00 |

Example 15 Transmembrance Transport Action of Polyethylene Glycol-Modified Series Compounds Caco-2 is an epithelial cell of human colon cancer, it may differentiate and grow on its own into epithelial cell monolayer having a structure and function similar to small intestine and represented with an active transportor and partial metabolic enzyme, and is a good model for evaluating in vitro membrane permeability. According to a standard culture procedure of the Caco-2 cell, a cell monolayer is prepared on a Transwell culture insert, a culture hole having a transmembrane resistance greater than 300 Ω·cm² is selected to perform a transmembrane experiment, and positive quality control drugs atenolol (which can penetrate the membrane difficulty) and methyltestosterone (which can penetrate the membrane easily) are selected in parallel to perform necessary quality control for the experimental system.

1. Unidirectional Transport Experiment

400 μL quality control drug (atenolol or methyltestosterone) or a drug to be tested is added respectively into holes of an upper pond of the culture insert, 500 μL Hank's liquid pre-incubated at 37° C. is added in a lower pond, incubation is performed in $CO_2$ incubator for 90 min, the solution of the lower pond is collected, quantitatively processed and measured to calculate its appearance penetration coefficient (Papp):

$$Papp=(dQ/dt)/(A \cdot C_0)$$

Wherein dQ is an accumulated penetration amount of a drug receiving pond with a measure unit μmol; dt is incubation time with a measure unit min; A is a diffusion area with a measure unit $cm^2$; $C_0$ is an initial administration concentration of an administrating pond with a measure unit $μmol \cdot L^{-1}$; Papp has a measure unit cm/s.

A universal standard for evaluating Caco-2 cell transmembrane transport penetration is that $Papp > 100 \times 10^{-6}$ indicates a compound which penetrates the membrane easily; $100 \times 10^{-6} > Papp > 10 \times 10^{-6}$ indicates a compound which penetrates the membrane at a medium level; $Papp < 10 \times 10^{-6}$ indicates a compound that penetrates the membrane difficulty.

2. Bidirectional Transport Experiment

An evaluation objective of the bidirectional transport is to preliminary observe that the transmembrane transport of the object to be tested has active transport procedure mediated by an efflux transporter. Positive quality-control drug digoxin and a drug to be tested are added respectively in holes of the upper pond or lower pond of the culture insert, Hank's liquid pre-incubated at 37° C. is added in an opposite pond, incubation is performed in $CO_2$ incubator for 90 min, the solution of the opposite pond is collected, quantitatively processed and measured to calculate its appearance penetration coefficient (PappA-B and PappB-A) according to the above formula and a ratio of the two; when the ratio is >2, it is prompted that the transmembrane transport of the compound might involve active transport mediated by an efflux transporter.

The experimental results of transmembrane transport are shown as follows:

| Compound | Papp(*10⁻⁶)A→B | Papp(*10⁻⁶)B→A | Papp(B→A)/Papp(A→B) |
|---|---|---|---|
| SMQT-01 | 10.55 ± 0.36 | 15.50 ± 0.06 | 1.47 |
| SMQT-02 | 9.87 ± 0.03 | 14.52 ± 0.12 | 1.47 |
| SMQT-03 | 6.25 ± 0.51 | 11.06 ± 0.21 | 1.77 |
| DSTN-51 | 8.55 ± 2.29 | 23.91 ± 1.24 | 2.80 |
| DSTN-42 | 4.57 ± 0.87 | 11.43 ± 0.72 | 2.50 |
| DSTN-62 | 6.44 ± 0.11 | 15.01 ± 0.59 | 2.33 |
| DZA-01 | 11.54 ± 0.36 | 15.50 ± 0.06 | 1.34 |
| DZA-02 | 12.32 ± 0.34 | 25.50 ± 1.21 | 2.07 |
| DZA-03 | 8.96 ± 0.35 | 23.67 ± 0.45 | 2.64 |
| DZA-04 | 6.76 ± 0.24 | 11.53 ± 0.58 | 1.71 |
| DZA-05 | 6.85 ± 0.46 | 23.87 ± 0.57 | 3.48 |
| DZA-06 | 8.86 ± 0.51 | 18.12 ± 0.32 | 2.05 |
| DZA-07 | 6.50 ± 0.06 | 25.88 ± 0.53 | 3.98 |

Example 16 Blood-Brain Barrier Permeability

The drug in plasma is enabled to reach a steady state by using a rat model in a manner of injection at an even speed, to see a ratio value (Kp value) of a drug concentration in the plasma and a drug concentration in brain tissue upon the steady state, to represent a distribution capability of the drug in the brain tissue. It is characterized by reliable data, direct provision of blood/brain distribution ratio value of the compound, and saving of animals and dosage.

Sumatriptan Series:

Research results show that the blood-brain barrier permeability of the three compounds is all lower than sumatriptan, wherein the blood-brain barrier permeability of SMQT-01 compound is 1/50 of sumatriptan, the blood-brain barrier permeability of SMQT-02 compound is 1/37 of sumatriptan, and the blood-brain barrier permeability of SMQT-03 compound is 1/13 of sumatriptan.

Dasatinib Series:

Research results show that the blood-brain barrier permeability of the three compounds is all lower than dasatinib, wherein the blood-brain barrier permeability of DSTN-42 compound is 1/18 of dasatinib, the blood-brain barrier permeability of DSTN-51 compound is 1/23 of dasatinib, and the blood-brain barrier permeability of DSTN-62 compound is 1/33 of dasatinib.

Dorzolamide Series

Research results show that the blood-brain barrier permeability of seven compounds is all lower than dorzolamide, wherein the blood-brain barrier permeability of DZA-01 compound is 1/55 of dorzolamide, the blood-brain barrier permeability of DZA-02 compound is 1/34 of dorzolamide, the blood-brain barrier permeability of DZA-03 compound is 1/65 of dorzolamide, the blood-brain barrier permeability of DZA-04 compound is 1/12 of dorzolamide, the blood-brain barrier permeability of DZA-05 compound is 1/28 of dorzolamide, the blood-brain barrier permeability of DZA-06 compound is 1/8 of dorzolamide, and the blood-brain barrier permeability of DZA-07 compound is 1/27 of dorzolamide.

Example 17 Experiment on Absolute Bioavailability of Polyethylene Glycol-Sumatriptan Conjugate Animal: male SD rat
Groups of the experiment: intravenous injection group and oral administration group, four rats being provided for each rat
Dosage: determined by a preliminary experiment
Administration manner: tail intravenous injection, intragastric administration
Blood sampling point: determined by a preliminary experiment
Data processing: an area under a curve is calculated for intravenous injection and oral administration by using a trapezoidal method, and a bioavailability is calculated by using the following formula:

$$F = \frac{AUC_{p.o.} \times Dose_{i.v.}}{AUC_{i.v.} \times Dose_{p.o.}} \times 100\%$$

Research results show that absolute bioavailability of SMQT-01 compound is 17%, absolute bioavailability of SMQT-02 compound is 23%, and absolute bioavailability of SMQT-03 compound is 25%.

The invention claimed is:

1. A drug-polyethylene glycol-drug conjugate of formula (I), the conjugate being formed by combining low molecular weight polyethylene glycol with two drug molecules,

TA-X-PEG-X'-TA'  (I)

Wherein:
PEG is a polyethylene glycol residue having the following structure,

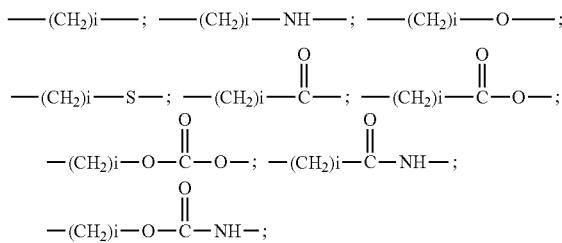

n is an integer of 0-25;
X, X' are linking groups which may be identical or different, selected from a group consisting of —(CH$_2$)i—; —(CH$_2$)i—NH—; —(CH$_2$)i—O—;
—(CH$_2$)i—S—; —(CH$_2$)i—C(O)—; —(CH$_2$)i—C(O)—O—;
—(CH$_2$)i—O—C(O)—O—; —(CH$_2$)i—C(O)—NH—;
—(CH$_2$)i—O—C(O)—NH—;

i is an integer of 0-10;
TA, TA' are target compounds that may be identical or different, selected from a group consisting sumatriptan, dorzolamide, irinotecan, camptothecin, dasatinib, paclitaxel, docetaxel, Dccyclovirobuxinum D, diethyl stilbestrol, estradiol, prazosin, terazosin, metoclopramide, ursodesoxycholic acid, rapamycin, scopolamine, and procaine.

2. The conjugate according to claim 1, wherein n is an integer of 0-10.

3. The conjugate according to claim 1, wherein i=2, and X, same as X', is —(CH$_2$CH$_2$)O—.

4. The conjugate according to claim 1, wherein TA is the same as TA' and selected from a group consisting of sumatriptan, dorzolamide and dasatinib.

5. A drug composition comprising the conjugate according to claim 1 and a pharmaceutically acceptable carrier or excipient.

6. A drug composition comprising the conjugate according to claim 1 and a pharmaceutically acceptable salt, wherein the pharmaceutically acceptable salt is selected from a group consisting of hydrochloride, hydrobromate, sulphate, nitrate, phosphate, citrate, tartrate, fumarate, maleate, lactate, benzene sulfonate, pantothenate, ascorbate or combinations thereof.

7. The drug composition according to claim 5, and wherein the drug composition is in the form of tablet, suppository, pill, soft and hard gelatin capsule, powder, solution, suspension or aerosol.

* * * * *